United States Patent
Zaltman et al.

[11] Patent Number: 6,099,319
[45] Date of Patent: Aug. 8, 2000

[54] NEUROIMAGING AS A MARKETING TOOL

[76] Inventors: Gerald Zaltman, Harvard University, Graduate School of Business Administration, Morgan Hall 190, Soldiers Field Rd., Boston, Mass. 02163; Stephen M. Kosslyn, 830 William James Hall, Harvard University, 33 Kirkland St., Cambridge, Mass. 02138

[21] Appl. No.: 09/188,796

[22] Filed: Nov. 9, 1998

Related U.S. Application Data

[63] Continuation-in-part of application No. 09/028,382, Feb. 24, 1998.

[51] Int. Cl.[7] .................................................. G09B 19/00
[52] U.S. Cl. .......................... 434/236; 434/362; 707/500; 707/530; 600/301; 600/306
[58] Field of Search .................................... 434/236, 238, 434/258, 362; 706/927, 45, 5, 16; 705/1, 2, 11; 707/500, 530; 600/301, 306

[56] References Cited

U.S. PATENT DOCUMENTS

| | | | |
|---|---|---|---|
| 5,243,517 | 9/1993 | Schmidt et al. | 434/236 X |
| 5,253,168 | 10/1993 | Berg | 364/413.01 X |
| 5,436,830 | 7/1995 | Zaltman | 707/530 |
| 5,613,498 | 3/1997 | Yasushi et al. | 128/731 X |

OTHER PUBLICATIONS

Bottini, et al., 1994. "The Role of the Right Hemisphere in the Interpretation of Figurative Aspects of Language. A Positron Emission Tomography Activation Study." *Brain* 117: 1241–1253.

*Primary Examiner*—Jessica J. Harrison
*Assistant Examiner*—Chanda Harris
*Attorney, Agent, or Firm*—Roberts, Abokhair & Mardula, LLC

[57] ABSTRACT

Neuroimaging as a means for validating whether a stimulus such as advertisement, communication, or product evokes a certain mental response such as emotion, preference, or memory, or to predict the consequences of the stimulus on later behavior such as consumption or purchasing. Subjects are exposed to stimuli of varying types. Their brain responses are then measured by any one or a combination of neuroimaging devices. The results of neuroimaging are then used to predict future behavior of the subject and those similarly situated with respect to purchase or consumption of products, based upon the non-subjective evidence of neuroimaging.

21 Claims, 6 Drawing Sheets

NEUROIMAGING AS A MARKETING TOOL

This application is a continuation in part of co-pending application Ser. No. 09/028,382 filed on Feb. 24, 1998, disclosure of which is herein incorporated by reference in its entirety.

FIELD OF THE INVENTION

This invention relates to an improved marketing research tool. Specifically, it relates to using neuroimaging to determine a consumer's response to marketing type stimulus.

BACKGROUND OF THE INVENTION

In today's highly competitive economy, a company's survival depends upon the marketing manager's ability to make sound business decisions, to outguess competitors, to anticipate consumer needs, to forecast business conditions and to plan generally for company growth. Marketing research is a tool used to accomplish these tasks. Such research is also vital in order to effectively monitor and evaluate past business decisions. A productive and thriving business will be one which suits the interests of customers, thus effective marketing begins with the recognition of customer needs.

It is well established that much communication occurs nonverbally (Weisner, 1988; Knapp, 1981; Seiter, 1987). That is, people "say" and "hear" a great deal more through nonverbal rather than verbal means of communication. However, virtually all market research tools rely on verbal means of communication such as questionnaires, telephone interviews, face-to-face interviews and discussions or focus groups. Such market research tools do not measure thought processes which are occurring without or below awareness. Indeed, even processes which the customer is aware of are often not measured well due to misreporting or under reporting for a variety of reasons.

Because companies rely so much on verbally oriented research tools they often miss much of what customers "say" and "hear" nonverbally. Thus, companies often miss important opportunities to understand customers better and to communicate better with them. As a consequence, companies miss opportunities to better serve their customers.

Similar to the situation of a company miscommunicating with its customers, communication within a company can be poor. This can be particularly true when the communication concerns thoughts and feelings about various personnel issues such as diversity, compensation, proposed or existing organizational arrangements such as merging and dividing debts, creating new organizational structures, interactions between superiors and subordinates and so on.

Lastly, self communication can also be an important issue; that is, how does the manager or C.E.O. think their customers think. These pre-existing biases can serve to "color" interpretations of marketing data. With awareness of these perceptions, one may more appropriately conduct market research.

A means for bringing to a level of conscious awareness those thoughts and feelings that are ordinarily not evident or are not evident in a clear or precise way is disclosed in U.S. Pat. No. 5,436,830 to Zaltman. Zaltman discloses a Metaphor Elicitation Technique (MET) which utilizes various research techniques to create a visually and other sensory oriented method and apparatus for creating research for marketing campaigns or to validate the thrust of an existing marketing campaign to determine if it accomplishes its stated purpose. This technique can also be used to improve inter-office and self communication. The disclosure of U.S. Pat. No. 5,436,830 to Zaltman is herein incorporated by reference in its entirety.

The process and apparatus of MET is based on the establishment of metaphors by users. A metaphor is the understanding and experiencing of one thing in terms of another. For example, a person may see a picture of an American flag as reflecting a sense of patriotism and hence be representative of his or her commitment to an American auto manufacturer.

The MET technique engages internal images, (neural patterns which underlie thought and feeling) and external images, (pictures, sounds, tastes, etc.) which represent or convey internal states of mind. It does this through a variety of steps and processes at each step. All sensory images are important nonverbal means of communication. Multiple sensory images are also important in the present invention since one sensory image such as sight can trigger the experience of another sensory image such as taste. This kind of connection among senses is known technically as synesthesia.

One outcome of the MET technique is a set of stimuli such as concepts or ideas which express important feelings and thought in the form of metaphors, among other things. These metaphors draw on all sensory perceptual systems, especially vision.

These concepts or ideas can then be used to develop a consensus map which is a diagrammatic metaphor for representing and understanding the preferences, opinions, and feelings of the user. It describes the thinking of a particular group of users such as customers, office personnel, or management, by synthesizing the mental models of individuals into an overall diagrammatic metaphor. It is, in fact, the major end product of the MET apparatus and process and is the guide to marketing staffs in the creation of advertising campaigns or formulating other marketing decisions and actions, to administrators in dealing with various personnel issues or to managers in unveiling pre-existing biases or beliefs.

Thus the MET technique and its apparatus is unique in how it engages the neural processes of thought and feeling and allows their expression in the form of metaphoric images which engage visual and nonvisual sensory systems.

The MET comprises the following steps:

Step 1. Storytelling. The user describes the content of relevant visual images and how they are associated with the research topic for that user. The images selected for the baseline series of images for evaluation for a topic under study.

Step 2. Sorting Task. The user sorts images into meaningful groups.

Step 3. Identifying and Recording Sensory Metaphors. The user identifies what is and what is not a good sensory representation of the research topic, in terms of sound, shape, tactile sensation, color, taste, smell or scent, and emotional feeling.

Step 4. Further Construct Elicitation. A formal interviewing process in which pictures and other sensory stimuli are used to understand user thinking about the research topic. The constructs elicited in this step augment those elicited in Steps 1–3.

Step 5. Most Representative Image. The user indicates which picture (from a given set of pictures) is most representative of the research topic (e.g., the meaning of luxury).

Step 6. Verbal Description of Missing Images. The user describes relevant pictures that he or she was unable to find or obtain and explains their relevance.

Step 7. Identifying Opposite Images. The user identifies pictures that describe the opposite of the topic (e.g., what is not luxury).

Step 8. Company Perceptions of Users. Using sensory metaphors, the user describes what a company and/or key people, e.g. car designers, sales personnel, etc. think of them. (This is important since a user's response to a company is also influenced by this perception.)

Step 9. Critical Message to the Company. The user describes the single most important message they want to convey to a company on the research topic. The user selects the sensory images that best reflect this message.

Step 10. Surprise to the Company. The user describes which of his or her feelings or thoughts on the topic a relevant company is least prepared to hear. The user selects the sensory images that best convey this information.

Step 11. The Mental Map. The user creates a map or a causal model using the constructs which have been elicited to express the user's overall thinking about the research topic.

Step 12. Creation of a Summary Image. The user with the aid of a technician creates a single, still image (visual) which best summarizes the meaning of the research topic.

Step 13. Creation of a Vignette or Mental Video. The user, with the aid of a technician creates a movie-like vignette or video expressive of the research topic. This is done using animation. (Note: Steps 12 and 13 typically provide different but complementary information)

Step 14. Creation of the Consensus Map. The diagrammatic metaphor representing the researcher's understanding of user thinking. It consists of the users' most important constructs and their interrelationships. It describes most of the thinking of most users. It is an integration of information provided by all users participating in a project. Special analytic techniques are employed with the data used to construct the consensus map to determine whether market segments or subclusters of users can be identified within the consensus map. Thus one submap within the consensus map may be especially descriptive of one subgroup of users and another submap especially descriptive of another group's thinking. This analysis enhances the value of the consensus map in developing a marketing campaign.

The MET Apparatus

In order to effectuate the steps of the MET an apparatus is provided whereby a researcher, in conjunction with each user participating in a given research project, obtains the information needed to create the ultimate consensus map. The apparatus comprises a file of digital images from which are selected a series of images used for the storytelling step (Step 1). The user is able to add images to this file.

A digital sound recording is made of the user's story telling. The MET apparatus appends the digital sound recording to the digital image. The (digital) voice recording contains what is technically called paralanguage. Paralanguage consists of tone, inflection, and other cues or factors relating to how something is said. These factors convey important meaning beyond the actual words used and may even contradict those words. Paralanguage is generally considered a nonverbal dimension of communication.

The Sorting Task (Step 2) is accomplished by designating and sorting the various images retrieved, again using automated means of designating the images into different groups. For example, a user can "designate" which pictures fit into a particular group or group designation via a cursor or other keyboard input means.

The Sensory Metaphor step (Step 3) can also be accomplished via the apparatus whereby a user selects from a file or bank of sensory images those that are most expressive of the topic. These sensory images are stored digitally and represent an array of sounds, colors, shapes, and descriptions of smells, touches, etc. The user is able to add descriptions to this digital file. These images are metaphors. A digital sound recording is made of the user's description/ selection of these images.

Step 1, 2, and 3 identify some important user constructs. Additional constructs are also elicited (Step 4) using a specific interviewing procedure. The sensory images or metaphors the user has identified in steps 1, 2, and 3 are used as the stimuli for this conversation. The MET apparatus contains these images as well as a procedure for conducting the conversation. This procedure involves a set of specifically designed thinking probes to help the user express their feelings, thoughts, and values.

The Most Representative Picture (Step 5) is also designated via the pointing/selection apparatus of the present invention.

Verbal descriptions of relevant images (Step 6) not available at the time of the interview are provided by a user. Verbal records of these images are stored in the system. These images comprise scenes/pictures designated by the user as providing additional information about the topic under study.

Opposite Images (Step 7) are also presented to or selected by a user based upon the user's statements. These images are stored on a separate database of digital images.

The user describes how he or she thinks a company involved with the research topic thinks of them (Step 8). Users may feel that they are thought of in negative or positive ways. Users select sensory images (visual, tactile, sound, etc.) from the image file or bank which they believe reflect how a company thinks of them. The user's voice (audio) is recorded digitally on the apparatus of the present invention as he or she provides this information and is connected to the appropriate image.

The critical message to the company (Step 9) and the surprise to the company (Step 10) are illustrated by the user using various visual and other sensory metaphors in the image file or bank. The user's verbal commentary is recorded digitally (in audio) by the apparatus and connected to the appropriate images.

The Mental Map (Step 11) is a series of recorded constructs or images created by the user and stored in the system. These mental maps constitute accurate representations of ideas important to the user and how they relate to one another. The set of constructs elicited through earlier steps are brought up on the display device of the apparatus. These are validated by the user. The user then establishes connections among the constructs using a mouse, cursor, or pressure sensitive digitizing tablet (using a stylus or even a finger.)

A composite or summary digital image is created next (Step 12) using a form of "clip art" common to many desk top publishing systems and an image management system stored in the CPU. A technician assists the user in the use of the software. A user's own pictures often form the starting point for this step. A digital voice recording is made of the user's explanation of this summary image and is appended to the image as part of the record.

The user's description of a movie-like vignette (Step 13) describing the research topic is recorded. That is, the user's voice is digitally recorded (as in earlier steps) as this vignette is described. The user then directs a technician in the creation of an animated representation of this vignette using standard computer video animation techniques. The user's digitally recorded (audio) description is appended to this vignette.

The final creation of a consensus map (Step 14) is essentially the summation of all of the data created by individual users using the apparatus. The consensus map contains verbal labels for each major construct. Constructs that are related to one another are connected with arrows. The researcher or marketing manager is able to click (with a mouse or other device) on a particular construct. When this is done the most relevant pictures and other sensory metaphors associated with that construct appear on the computer screen or other display device. Where appropriate, the digitally recorded voices of users commenting on the pictures or other sensory metaphors are also presented. The researcher or marketing manager may also click on an arrow connecting any two constructs and retrieve a verbatim text and/or audio statement from one or more users describing how one construct affects the other.

The researcher or marketing manager is also able to review all animated vignettes created in Step 13. These vignettes are indexed to constructs in the consensus map and to their interrelationships. Thus, it is possible to see and hear an animated enactment of a construct and its impact on other constructs.

The metaphors associated or connected with each construct are the sensory definitions of those constructs. They convey the important nonverbal meanings of these constructs. It is these meanings which are often missing from market research. This is partially due to the fact that verbal skills of those whose input is being solicited vary widely. It has been found however that in employing the MET, the verbal skills of a user are not critical since the visual sensory development of persons is relatively more advanced than verbal development. Therefore, education level and/or age of a user is not critical to the MET. Generally users using the MET are more equal on a sensory level than they are on a verbal skills level. This in turn contributes to the accuracy and consistency of responses generated.

The MET presently runs on the Apple Macintosh family of computers. However, the MET can also be implemented on IBM and IBM compatible computers employing the Intel® 80386, 80486 or Pentium family of processors, although this is not meant as a limitation. Input scanners such as the Apple OneScanner Polaroid CS-5000 Photo Print Scanner, the Microtek ScanMaker 1850S (35 mm slide/negative scanner) and the Microtek ScanMaker 6007S flatbed scanner are all appropriate scanners for use with the present invention. Other scanners having similar capabilities are clearly appropriate.

Other input devices include the WACOM SD420E Digitizing Tablet for shape input and to delineate portions of images to be extracted as well as the CALCOMP Drawing Board Roman II Digitizing Table for the same purpose.

Additional output devices include the LaserMaster 1000 and the GSC ColorFast Digital Film Recorder for providing hard-copy output of images created.

It is desirable to further refine the information obtained through practicing the MET technique. That is, once the key constructs and important metaphors have been identified, it is useful to assess them further. For example, what is their relative importance? Do they produce responses that people may have trouble articulating orally or using paper and pencil measures such as questionnaires? Do they produce responses that people are not aware they are experiencing? Are some of these constructs and metaphors more memorable than others? Are some more positive (negative) than others? It is also desirable to use neuroimaging to evaluate marketing stimulus, both directly and indirectly. This refinement is the subject matter of the present invention.

SUMMARY OF THE INVENTION

It is therefore an object of the present invention to provide a method for augmenting the Metaphor Elicitation Technique by using techniques that monitor physiological functioning.

It is a further object of the present invention to monitor physiological functioning through the use of functional magnetic resonance imaging, positron emission tomography, magnetoencephalography, galvanic skin response or conductance, event related potentials, heart rate changes and/or single photon emission computer tomography.

It is a further object of the present invention to monitor the brain activities which underlie uncovered thoughts.

It is a further object of the present invention to monitor brain blood flow as a function of marketing related stimuli.

It is yet a further object of the present invention to monitor brain blood flow through either the use of positron emission tomography (PET), functional magnetic resonance imaging (MRI) magnetoencephalography (MEG) and/or single photon emission computer tomography (SPECT).

It is yet a further object of the present invention to use neuroimaging to evaluate the effect of marketing stimulus, both directly and indirectly.

It is yet a further object of the present invention to use neuroimaging to evaluate advertising copy, consumer situations or potential behaviors.

It is yet a further object of the present invention to use neuroimaging to validate a questionnaire.

It is yet a farther object of the present invention to use neuroimaging to predict consumer behavior in response to marketing stimulus.

DETAILED DESCRIPTION OF THE PREFERRED EMBODIMENT

Figure 1:
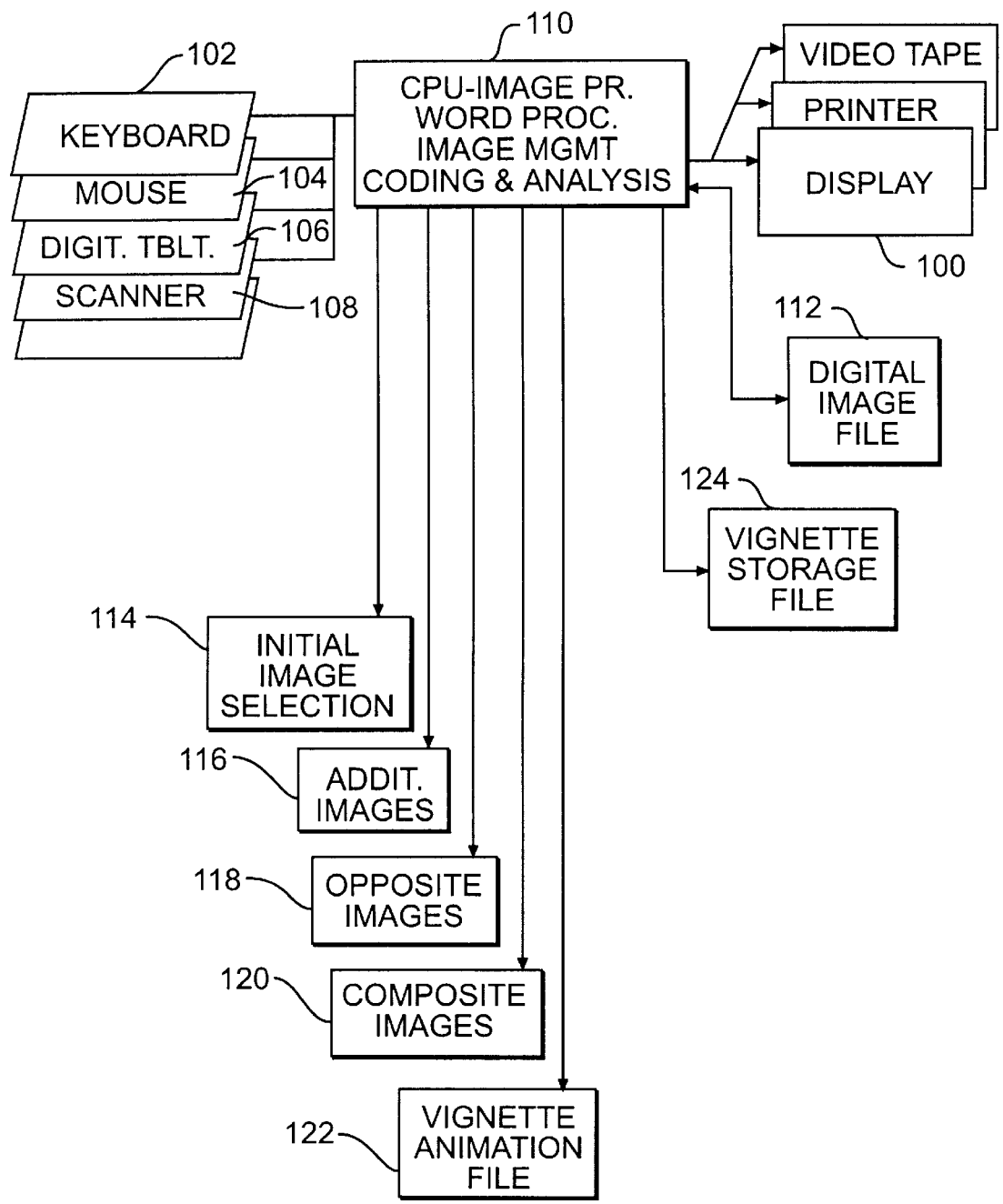
FIG. 1 illustrates the system architecture of the present invention.

Referring to FIG. 1, the MET apparatus is described. The apparatus comprises display 100 for displaying alpha numeric data as well as the various images viewed by a user. The apparatus further comprises keyboard 102, mouse 104, pressure sensitive digital tablet 106, and scanner 108, for reading slides, negatives, and pictures into Central Processing Unit (CPU) 110 for inputting data and designating images or sections of images which are to be used in the creation of composite images or to merely designate those images to be stored.

CPU 110 comprises various logic whereby input commands can be received from keyboard 102, mouse 104, and pressure sensitive digitizer tablet 106 to designate various images for subsequent processing and storage. CPU 110 comprises image processing/management software for cutting and pasting portions of images from one into another as well as to allow the input of alpha numeric data. CPU 110 also comprises file management software allowing digital images to be received, displayed and stored. It also comprises file management software for computer animation. CPU 110 also contains software for coding and analyzing constructs, sensory metaphors, still images, vignettes, and certain aspects of users' verbal language digitally recorded or entered by the researcher as written text. CPU 110 contains additional software that creates tables, graphs, consensus maps, and other analyses unique to MET and required for reporting research results. CPU 110 also contains software which helps guide the researcher and users through the sequence of steps and through the activities within each step.

Digital image file 112 comprises a large library of digital images from which are selected images for the initial groupings and subsequent images as required for a user during the course of any given study. This file includes visual images as well as those relating to the several other senses (Step 3).

The MET system also comprises a series of temporary storage files in which are stored initial images 114 selected for evaluation, additional images 116 selected by a user for use in the verbal image (Step 6), opposite images 118 for use in the description of those images which are opposite to the concept being evaluated (Step 7), composite image file 120 in which is stored the digital image created by the user (Step 12), vignette animation file 122 comprising parts of all other images selected and temporarily stored as a file of images for use in the creation of a vignette (Step 13), and vignette storage file 124 for storing complete vignettes.

During Step 1, the user is asked to describe the salient contents of each picture displayed. These salient or relevant characteristics are stored. The pictures are presented to the user during Step 1, on the video display of the present invention. During this and other stages, the user's verbal comments are audio recorded digitally, in the computer control processor.

During Step 2, the user is asked to sort the pictures into meaningful categories and provide a label or description for each category. There are no restrictions as to the number of categories or the number of pictures in each category. This sorting task helps establish the major themes or constructs relevant to a particular user. In addition, the sorting task is used as a precursor to Step 4, the further elicitation of constructs using probing interviewing.

In Step 3, the user is asked to describe what are and what are not good sensory representations of the research topic. For example, people often use their senses to describe their experiences, thoughts or emotions. Thus, this step elicits from a user what is and is not the taste, touch, smell, color, and sound of the concept being explored. In addition, the emotional feeling associated with the topic is also elicited. These sensory thoughts are recorded by the present invention during this step of the process.

In Step 4, the user is engaged in a discussion with the researcher which results in the elicitation of additional relevant constructs. The stimuli used for the elicitation of additional constructs are the pictures, picture groupings, and other sensory images identified and selected in steps 1 through 3. The elicitation of constructs is facilitated by the use of probing interviewing techniques designed for MET.

In Step 5, the most representative picture is selected from the group of pictures initially provided by the present invention during Step 1 and augmented by pictures the user brings to the researcher. The picture selected is that which is most expressive or representative of the assigned topic. It is important to note that this picture is often used as a starting point for the summary image of Step 12 (to be discussed below).

During Step 6, other images are recalled from the memory of stored images of the present invention. These pictures are those which are deemed relevant by the user to the topic being described. This step is critical since the pictures originally shown to the user may not be those most appropriate given that user's background and perception. Also, pictures the user wanted to bring to the meeting with the researcher may not have been available to the user. These additional images are also relevant to the Step 12 development of the summary image.

During Step 7, opposite images are selected by a user. Research has shown that any concept or construct contains a reference also to its opposite meaning. The user is thus asked to retrieve pictures that might describe the opposite of the topic being studied. For example, if the original assignment concerned the meaning of "coffee as a morning wakeup beverage," the user is asked what pictures would not reflect the concept of coffee as a morning wake up beverage. Such pictures are selected from the file of stored images in the present invention and subsequently stored as a response of that particular user.

Step 8 provides the user an opportunity to describe how he or she thinks the companies involved with a certain product think of their users. The user illustrates these thoughts with images from the present invention. Market research tools are almost always focused on eliciting what users' think of a product, brand, or company. While this is important, a person's response to a service provider or to a product also depends on how they feel they are perceived. Thus, how a user or patient believes an HMO's physicians or other staff think of them will influence that person's decision to use that HMO and, if they join, will also influence their use of medical services.

Step 9 enables the user to identify the most important thought he or she has which the user feels a company should understand. The sensory images associated with the thought are selected by the user (from within the apparatus) to help convey his or her thinking.

Step 10 identifies information that the user thinks will be surprising to a company, i.e. information that the user thinks the company is least prepared to hear. This provides additional perspective about how well informed users feel companies are about their needs. Here, too, users' thinking is clarified by the use of sensory images drawn from the present invention.

Step 11 is the creation of a mental map or model involving the constructs of the person viewing the pictures. The user reviews all of the constructs recorded by the present invention and verifies that they are accurate or whether there are important ideas missing from the list of constructs. These constructs are then graphically linked to one another based upon relationships established by the user and stored by the system. This forms the mental model, or the mental map.

This map is entered into the central processor unit. The user provides a brief description of the map which is audio recorded digitally in the computer.

After completing the mental map, the user creates a summary image or digital montage which expresses the topic under study (Step 12). This is done using the images already selected together with the graphical ability of the present invention to combine images or portions of images to create a single summary image. All of the pictures selected by a particular user are stored in the computer. Additional images are also available from the stored file of images of the present invention. During this step, the user can use one picture as a background for the new image, add elements from other pictures, and augment these with new art work. Using image processing and manipulation techniques, the user can rearrange and alter the subject, the foreground, the background, or specific elements including color, object size, shapes, positions, and even textures appearing within an image to be more expressive of the concept under study. For example, a person dressed in a particular way may be expressive of a particular automobile concept. Such a person captured in one photograph can be "cut" moved to a clip board, resized, placed at a different angle, and have the color of clothing changed, and then "pasted" electronically onto another picture containing other meaningfull information. The "cut-out" image could also come from a tool box or collection of pictures maintained in the separate image file. The user's description of the significance of this image is audio digital recorded and made a part of the picture file. This image can also be printed or recorded on film to create a hard copy record of the picture created.

After completing the summary still image (Step 12) the user next describes a movie-like vignette or video in which action or motion is involved (Step 13). Thus a user describing coffee as a morning wake-up beverage may describe someone in a farm setting, walking to the road to get the newspaper from a mail box, the sun rising, a rooster crowing in the background, and the same person returning to enter a kitchen where a mug of steaming hot coffee is waiting. This vignette is readily created using computer animation techniques and may require less than one minute to play when completed. The user's description of the significance of this vignette is audio recorded digitally and made part of the vignette.

The information provided by steps 12 and 13 complement one another and often produces new constructs and/or new insights about previously identified constructs.

The final step in the process (Step 14) is the creation of the consensus map by the researcher. The images and constructs elicited during use of the present invention, the development of each user's mental model, and the digitized images created provide the data base from which the consensus map is generated. The consensus map describes a) most of the thinking of, b) most of the people, c) most of the time. Thus the data from all users are aggregated and developed into a consensus map.

This consensus map contains the most important set of constructs that influences user perception, understanding and behavior. These constructs are then used to guide the development and implementation of a marketing campaign for a particular product.

Figure 2:
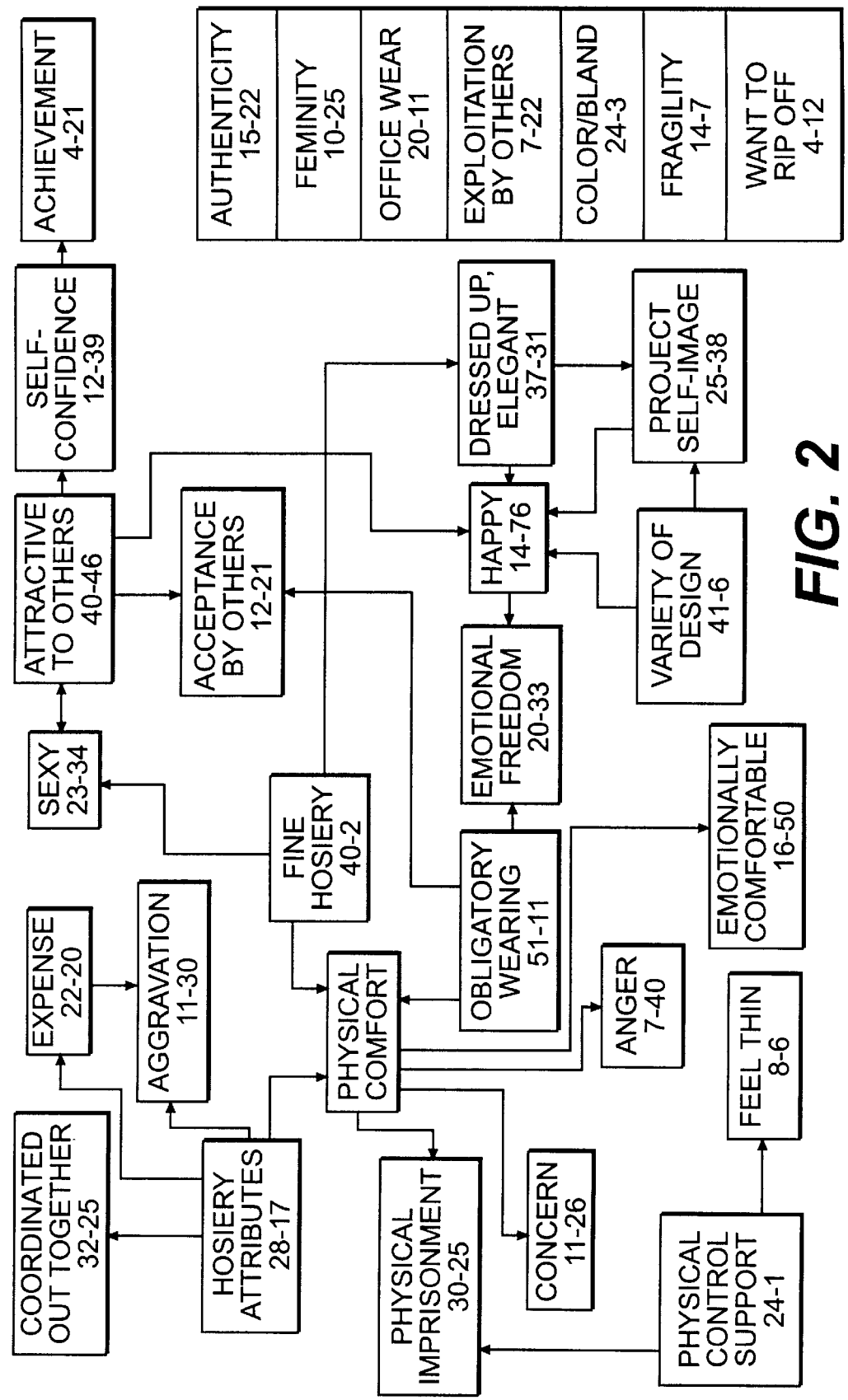
FIG. 2 illustrates a consensus map example.

FIG. 2 shows an example of a consensus map. In this example, the subject product was hosiery. Various constructs directed toward the hosiery were elicited from the participating subjects. Some construct examples shown in the figure are self-confidence, emotional freedom, and aggravation. In all, thirty different constructs were mentioned by at least ten of the 25 subjects. Sometimes a subject noted a relationship between two or more of the constructs mentioned. For example, some subjects linked the construct of self-confidence to the construct of achievement, meaning that those subjects considered these distinct attributes related.

Of the thirty constructs mentioned by at least ten of the subjects, 23 were mentioned at least five times as being related to another construct. The 23 constructs are shown drawn within ovals in FIG. 2. Arrows are shown drawn between these ovals. The oval from which the arrow originates contains the construct which is the origination point in that construct's relationship with the construct resident in the oval upon which the arrow terminates. The originating construct is the attribute which the subject felt was the cause of the second construct. For example, some women thought that the construct of expense involved in wearing hosiery led to a construct of aggravation. In some cases, the arrow points in both directions between constructs.

Beneath each construct are two numbers separated by a hyphen. The number to the left of the hyphen indicates the number of times this construct was the origination point in the relationship with another construct. The number to the right of the hyphen indicates the number of times this construct was the destination point in a relationship with another construct.

The seven constructs listed in the rectangular box on the right side of FIG. 2 complete the original thirty constructs that were mentioned by ten or more of the 25 subjects.

How To Use

When a particular study is to be done concerning a topic, the market researcher initially selects a series of images for a user to view. These images include those a user brings to the meeting. This initial story telling (Step 1) provides basic images that describe the concept being evaluated.

The user next sorts the images by designating on the display screen which images fall into a user defined series of groups. This sorting task (Step 2) is done with the aid of a cursor, mouse or a stylus using a pressure sensitive digitizer tablet. The activated cursor selects the image.

During the sensory metaphor step (Step 3) the user again uses the cursor, mouse or pen-like stylus to identify what are and are not good sensory representations of the research topic. Again, the user may augment the existing file of sensory representation with their own sensory definitions.

During Step 4, the three visual images are selected randomly and their similarities and differences are explored using special techniques. The interviewing technique probes for basic meanings and connection to the research topic. The selection of groups of three images continues until the various associations amongst the images are defined.

During Step 5, the user again through use of a cursor mouse or stylus pen indicates which is the most representative picture of the research topic.

Thereafter during Step 6, the user is allowed to retrieve additional digital images from digital image file 112 which may not have been in the original group of images displayed to the user. The relevance of these images is then recorded via alpha numeric input.

The user is next directed by the apparatus during Step 7 to retrieve images which describe the opposite of the topic being studied. These images are retrieved and appropriately stored.

During steps 8, 9, and 10 the user describes how they believe companies think of them (step 8), what the most important thought is they would like to convey to companies involved with the product or service being studied (step 9), and what they believe these companies would be most surprised to learn about their user's thinking (step 10). Sensory images associated with this information are selected or described by the user. These images are appropriately stored. The user's descriptive comments about these sensory images are also recorded using digital audio. Thus during a play back, the sensory image is brought to a display screen and the user's voice is heard describing the relevance of that image.

During Step 11, the user creates a graphical model of his or her thinking using the various constructs which have been elicited during the course of the analysis. This is accomplished via graphical and image programs stored in the CPU.

During Step 12, a summary digital image is created whereby a user can cut and paste various portions of the different images collected into a montage or summary image depicting the concept being studied.

During Step 13, a movie-like vignette is created whereby the user is able to create an animated representation of their thinking. Standard procedures are available to accomplish this. The animation is stored in the CPU along with an audio description of the animation provided by the user.

Finally, during Step 14 the apparatus is used to diagrammatically represent the understanding among users of the concept being studied and the relevance of the images revealed during the course of that study. From this information an approach to a marketing activity is then derived. The apparatus of this invention connects each verbal construct in the consensus map with representative visual and other sensory images. This provides marketing managers with far richer data than do other techniques and thus permits more effective marketing programs.

As mentioned, the techniques described in this specification are not limited to marketing analysis. For example, the field of social network analysis is also amenable to the application of the techniques described herein. Instead of visual metaphors for products, visual metaphors for people, organizations and positions within organizations would be elicited from users. The output, or consensus map, would depict the various constructs and relationships among them as they relate to organizational or social network structure. These in turn would describe the strength of relationships and the attributes of particular individuals or groups of individuals within an organization. In the case of a vacant position, the user would visually describe the attributes of the ideal person needed to fill such a position to name but a few such applications of the MET.

MET Monitoring

By monitoring the physiological functions of the user, further insight can be obtained regarding the topic under consideration. Monitoring techniques can include functional magnetic resonance imaging, positron emission tomography, magnetoencephalography, galvanic skin response or conductance, event related potentials, heart rate changes and/or single photon emission computer tomography. From brain imaging measurements, inferences can be made about the function of specific regions of the human brain and how the integration of activity of geographically separate brain structures facilitates the psychological process under study. Evidence indicates that the brain is composed of a series of function-specific substructures; see, for example, Wet Mind, Kosslyn & Koenig (1992) which is herein incorporated by reference in its entirety. The organization within and between these substructures facilitates the spectrum of perceptual, cognitive and behavior production capacities accessible to an individual. A given psychological process such as forming a mental image, recalling a memory, solving a reasoning problem or generating an emotional response, requires increased or decreased processing within specific subsets of brain regions. Where there is increased processing within a brain region there must be a proportional increase in the concentration of oxygen and other blood-born metabolites accessible to that brain region. Thus, measuring the concentration of blood flow to the brain while an individual performs an isolated cognitive task provides a means of measuring the relative processing contribution of each subregion to the task.

In this fashion, the occurrence of unconscious processes—mental states involving feelings and thoughts people are unaware of—can be observed using techniques that monitor blood flow and other activity in various parts of the brain. For example, we know that when people are listening to a voice describing an automobile dealership, there is increased blood flow in the primary and secondary visual areas of their brain. This indicates that they are visualizing the dealership setting even if they may not recall that they are doing so. Additionally, when a positive description—based on the metaphor elicitation technique—is read to the subjects, the left dorsolateral prefrontal cortex is especially active. When a negative description is read—again based on what is learned from MET—the right dorsolateral prefrontal cortex is especially active. Research has shown an association between the following: the superior temporal gyrus and the processing of sounds; the posterior cingulate and fixating attention to a stimulus; area 19 and associative memory; inferior temporal cortex and visual recognition; parahippocampal and memory; precuneus and posterior parietal cortex and spatial mental imagery; anterior insula and negative emotional reactions; area 17 and visual processing; and areas 17, 18 and 19 and processing images generated during visual mental imagery.

Several means for monitoring brain activity are known to those skilled in the art. One such means is positron emission tomography (PET). PET is the tomographic imaging of local metabolic and physiologic functions in tissues, the image being formed by computer synthesis of data transmitted by positron-emitting radio nuclides, often incorporated into natural biochemical substances and administered to the patient. A computer traces the path of photons and produces a composite image representing the metabolism level of the tissue. The major advantage of PET is that it can show changes that occur fairly quickly, on the order of seconds.

In practice, during a PET scan, the subject inhales or receives via injection a trace amount of radioactive oxygen, (such as $O^{15}$) radioactive carbon, or a radioactive form of glucose, (such as fluorodioxyglucose with fluor-18) while he or she is engaged in the psychological task. The radioactive tracer passes through the circulatory system, and up into the brain. The more active a part of the brain is during the task, the more blood and blood-born products are delivered to that area. Hence, more radioactively tagged tracer materials are present in areas that were more active while the task was being performed. The PET scanner is equipped with a series of radiation detectors which quantify the level of radiation in a 3-D space. After the scan is completed the information from the PET scanner is analyzed by a program which maps the region-specific levels of radiation onto the topology of the brain. The result is an image of the brain that depicts the differential blood flow during the performance of the task and a set of statistical values that indicate the significance of the blood flow to each region.

SPECT is another, less expensive means of tomographic imaging metabolic and physiologic functions in tissue. Here, an image is formed by computer synthesis of data transmitted by single gamma photons emitted by radionucleides administered in suitable form to the patient. The isotopes used are of a lower energy, and can be stored on site. The result is an image with lower resolution and less detail, at a lower cost.

A second exemplary means of brain monitoring is functional magnetic resonance imaging or fMRI. fMRI uses nuclear magnetic resonance technology, in which the patient's head is placed in a magnetic background field and the nuclei of hydrogen atoms are excited by radio-frequency pulses at angles to the field's axis. After the pulses are completed, the atoms move to become realigned with the background magnetic field. The resulting signals vary in strength where hydrogen is in greater or lesser concentrations in the body, and are processed through a computer to produce an image. Oxygenated blood has different magnetic properties than blood in which the hemoglobin has been stripped of its oxygen. As a brain area does more work, it draws more oxygenated blood to it; in fact, more oxygenated blood arrives than can be used, and this accumulation of oxygenated blood produces the signal recorded during the most common method of fMRI.

Other fMRI methods such as magnetoencephalography, magnetically "tag" blood, so that the amount of blood flow to different parts of the brain can be tracked. A common factor to each of these methods is that they allow researchers to assess which parts of the brain are relatively active while a subject performs a task.

In practice, a person creates a digital image summarizing their key thoughts and feelings using the metaphor elicitation technique as described above, the person is then placed in a device which monitors physiological functioning. In a preferred embodiment, brain activity is monitored, although skin response and heart rate can also be monitored. Where brain activity is to be monitored, the user is placed in PET scan, fMRI, SPECT or MEG device as appropriate.

The person then reads and/or views and describes again his or her digital image. As this external image about a product or service is engaged by the person, the brain activity monitoring device records differential activity in various parts of the brain. This process provides special insights about the relative importance of the ideas represented by the digital image based upon the cognitive functions performed by specific areas of the brain. In a preferred embodiment, the monitored brain activity is recorded electronically.

Software is required to capture and analyze this brain activity. This software is generally known to those skilled in the art and includes Statistical Parametric Mapping (SPM) as developed by Karl Friston and colleagues at Hammersmith Hospital in London, U.K. SPM software allows one to transform the images from the subject's brains to a normalized size and shape based on the coordinates of Talairach and Tournoux (1988) and then to contrast conditions by summing over the entire group of subjects and subtracting the sum of one condition from that of the other. The result is a color map where more intense colors, such as red and white, indicate stronger activations. The activations are measured by a Z-score associated with each pixel in the contrast image.

In alternative embodiments, monitoring the physiological functions of the user can take place throughout, or at any time during, the metaphor elicitation technique.

In additional alternative embodiments, neuroimaging is used to validate marketing materials such as questionnaires, surveys, advertising, etc.

In still additional alternative embodiments, neuroimaging is used to determine a consumers response to marketing input, such as but not limited to advertising copy, consumer situations, potential behaviors, or questionnaires, and/or to predict consequences of the marketing input on later behavior.

Direct Evaluation of Stimulus Materials

Figure 3:
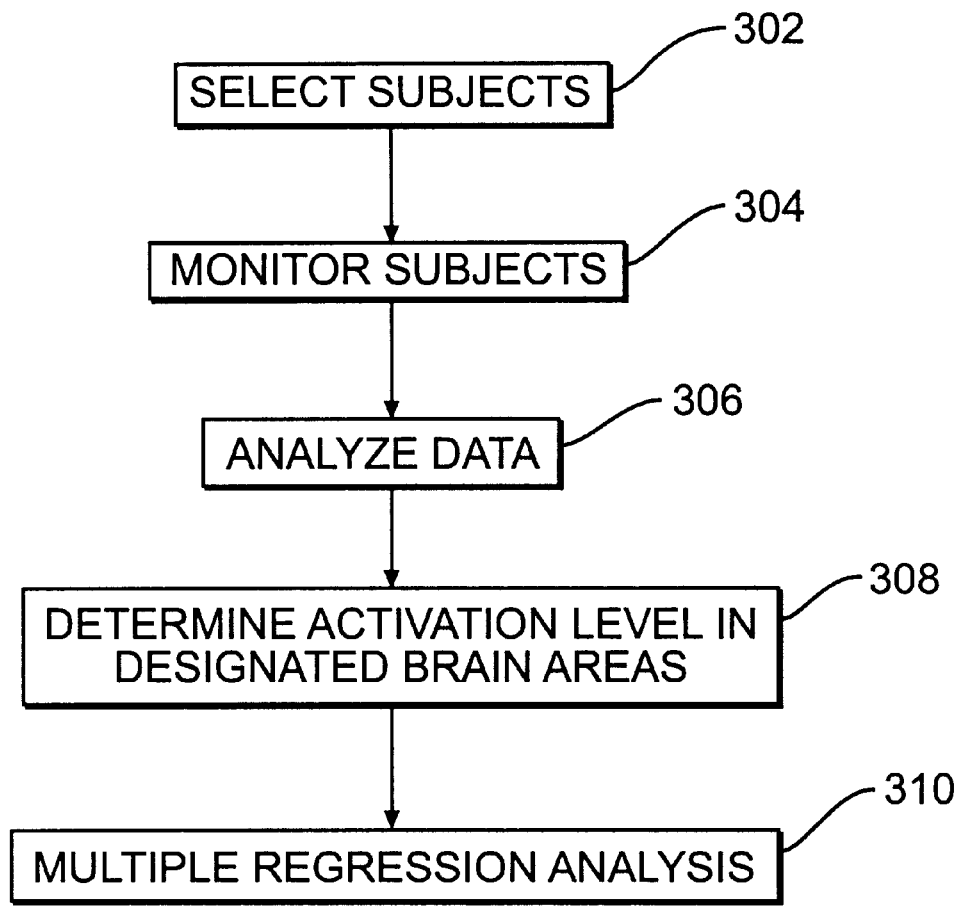
FIG. 3 illustrates the steps involved in direct evaluation of stimulus materials.

FIG. 3 illustrates the method used in direct evaluation of stimuli materials that can include but are not limited to advertising copy, consumer situations, communication, or product. This method is designed to validate whether certain stimulus materials evoke certain mental responses such as affecting emotion, preference and memory. Subjects are selected 302 to be representative of a particular segment of the market. Thus, subjects are selected 302 on the basis of various characteristics, including but not limited to age, income level, gender, education, and place of residence. Results are thereby targeted to specific segments of the market.

Subjects are monitored 304 in a neuroimaging device while they are exposed to a stimulus communication. Neuroimaging devices include but are not limited to PET, fMRI, MEG, and SPECT. These devices all provide measurements of how active various brain areas become while the subject is exposed to a stimulus. The stimulus can be visual or auditory, or a combination of the two. Examples of stimulus which can be used include: copy from an advertisement; a description of a hypothetical or actual environment or situation; or a description of a hypothetical or actual behavior that the subject is asked to imagine performing. The subject can be asked to evaluate the stimulus in some way when it is presented, including but not limited to providing a numerical evaluation of the subject's emotional reaction to the materials (e.g., on a seven-point ratings scale), deciding whether or not it is appealing, or deciding whether or not it is feasible. The subject may also be asked simply to view or hear the stimulus. At specified time periods after the scan (ranging from one week to several months), the subject is tested for his or her memory and feelings about the stimulus materials. This can include questionnaires filled out by the subject after each scan, or after each series of scans. The questionnaires probe memory, preference, and affective response. In addition, the subject's actual behavior, such as purchasing behavior for the product or visits to a specific environment, is recorded.

The neuroimaging data are analyzed 306. Activation in brain areas known to signal memory, preference and affective response is noted 308. The estimates of activation from each subject's brain are normalized, and then for each brain the local differences from the mean value are computed for brain areas thought to be relevant for the task (e.g., for registering emotional responses, attending to details, remembering the information). The presence of activation in particular brain regions, and in sets of regions, is evidence that the person had a particular cognitive and/or emotional response to the stimulus. For example, activation of the hippocampus is evidence that the communication is being stored in memory; activation of the left dorsolateral prefrontal cortex is evidence that the subject had a positive response to the materials, whereas activation of the right prefrontal cortex or amygdala is evidence that the subject had a negative response to the materials; and activation of the anterior cingulate or thalamus is evidence that the subject was paying close attention to the stimulus. This form of evidence does not depend on the subjects' conscious knowledge or opinions, and thus circumvents problems with various questionnaire-based approaches.

To validate the inferences based on brain activation, the brain activation values are then treated as independent variables in multiple regression analyses 310. The dependent variables are the behavioral measures collected at different periods after the scan. The dependent variables are regressed onto the independent variables. The goal is to discover which patterns of activation in brain areas best predict the subject's later memory, affect, or behavior.

The results are brain-based, non-subjective evidence that the communication will be likely to be memorable, lead to a specific emotional response, and/or likely to lead to a specific behavior.

After validation, brain responses alone are sufficient to evaluate the later memory for, emotional reaction to, and behavior concerning, the stimulus materials.

Indirect Evaluation of Materials

Figure 4:
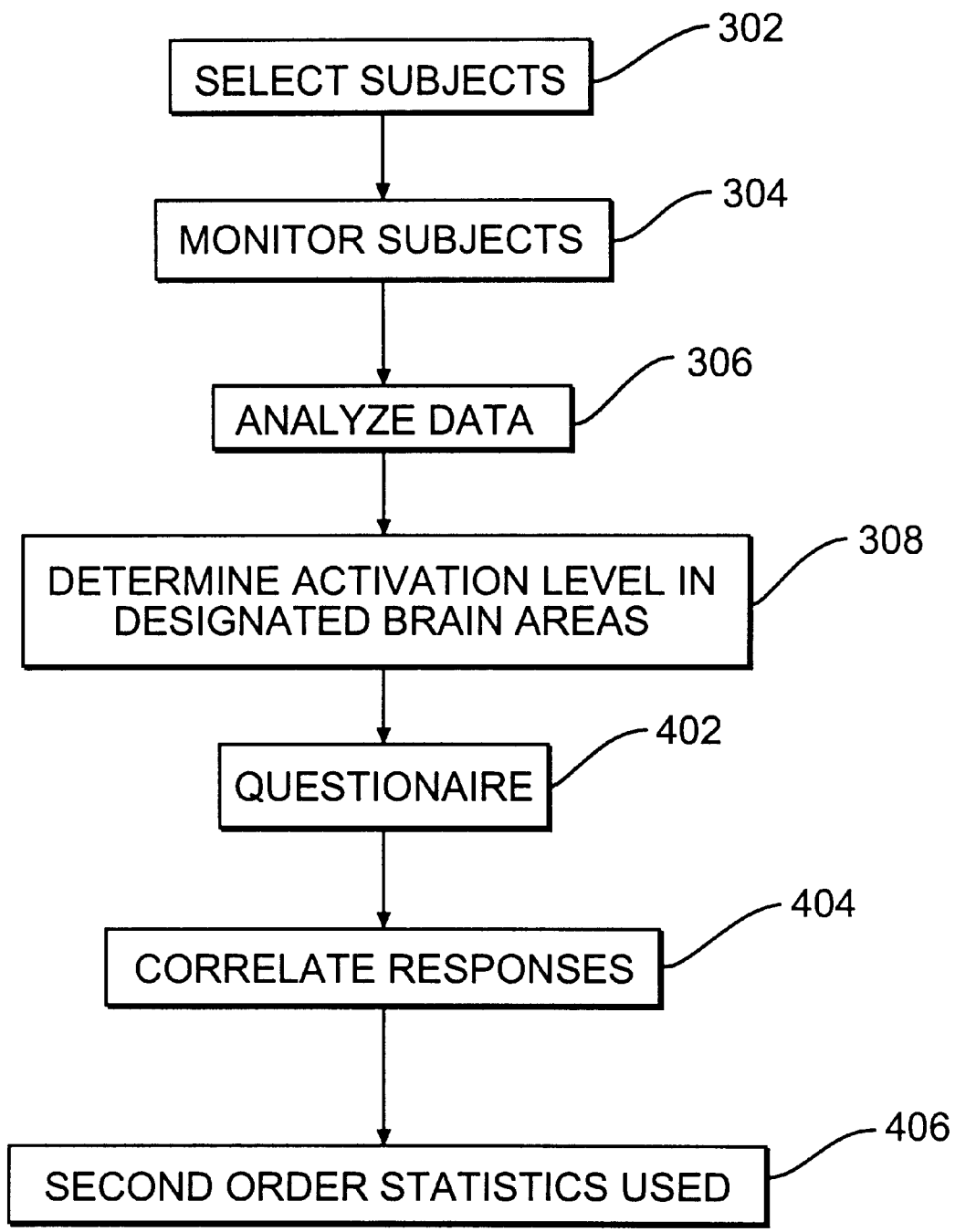
FIG. 4 illustrates the steps involved in indirect evaluation of stimulus materials.

FIG. 4 illustrates the method used in indirect evaluation of materials such as validating items on a questionnaire so that they can be used in lieu of the neuroimaging technique for evaluating similar materials.

Subjects are selected 302, subjects are monitored 304, data is analyzed 306 and activation in brain areas know to signal memory, preference and affective responses is noted 308, as is done in direct evaluation of materials and as is described above.

The subject then fills out a questionnaire after the scan 402. The questionnaire can include but is not limited to ratings of emotional response to relevant items, questions about common activities, questions about past experiences with relevant products, and so on. Responses to the questionnaire can be timed, and the latencies can also be used as part of the analysis.

The responses to each item on the questionnaire are correlated 404 with measures of brain activation. To the extent that the brain activation predicts later memory, emotional response, and behavior, the responses to specific items on the questionnaire that are highly correlated with those brain responses will also predict these variables.

Second-order statistics can be used to provide acceptable correlations 406. Such statistics include but are not limited to difference scores between items, and inter-item correlations. These correlations reveal which items on a questionnaire are valid; that is, responses to these items serve to predict brain responses.

After validation, the questionnaire can be used to evaluate similar materials for that segment of the market. Each new class of stimuli, or each group representing a market segment, should be examined using neuroimaging and appropriate questionnaires to be appropriately validated.

Predicting Consequences of an Advertisement or Communication on Later Behavior

Figure 5:
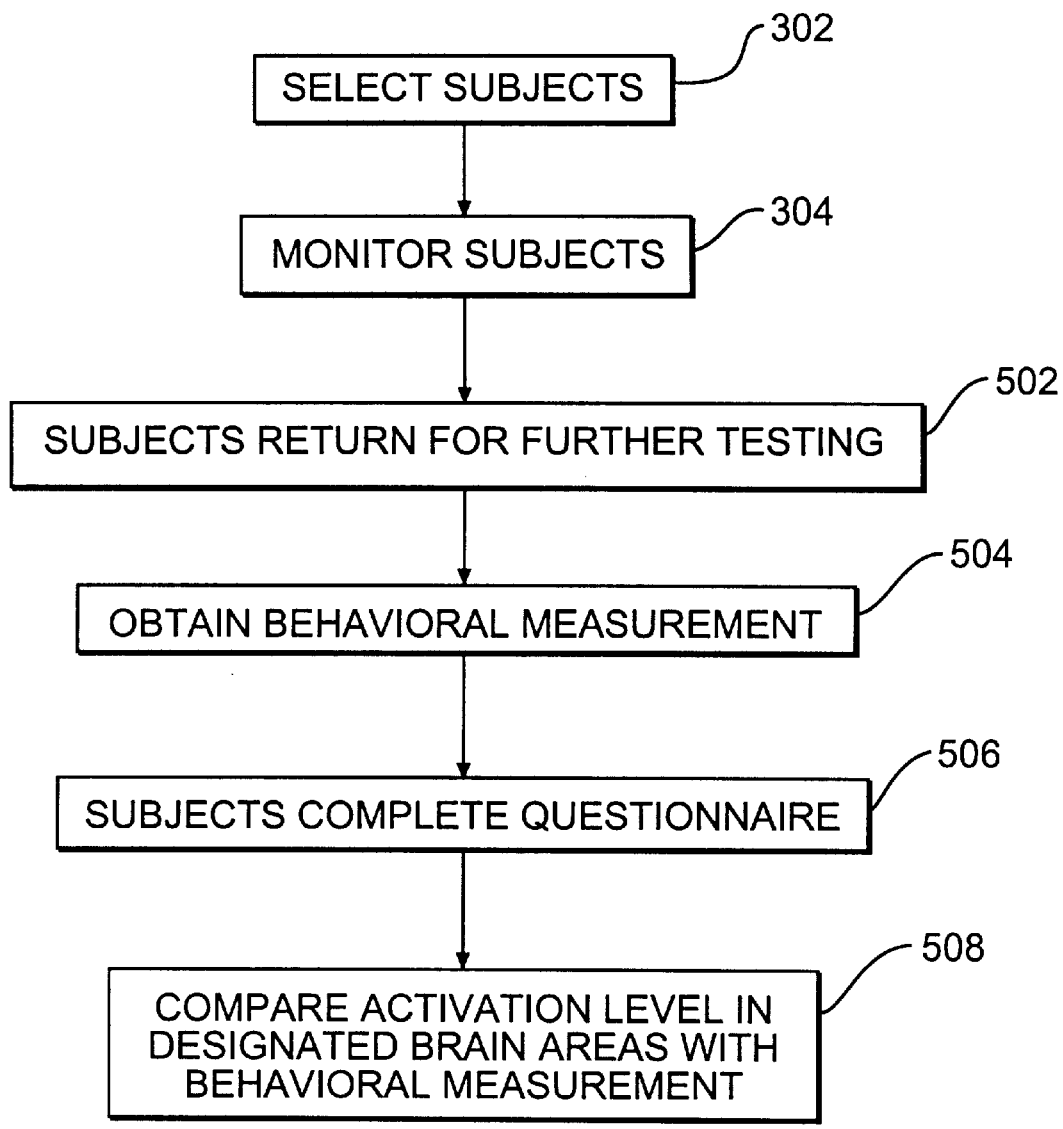
FIG. 5 illustrates the first phase of a prediction method.
Figure 6:
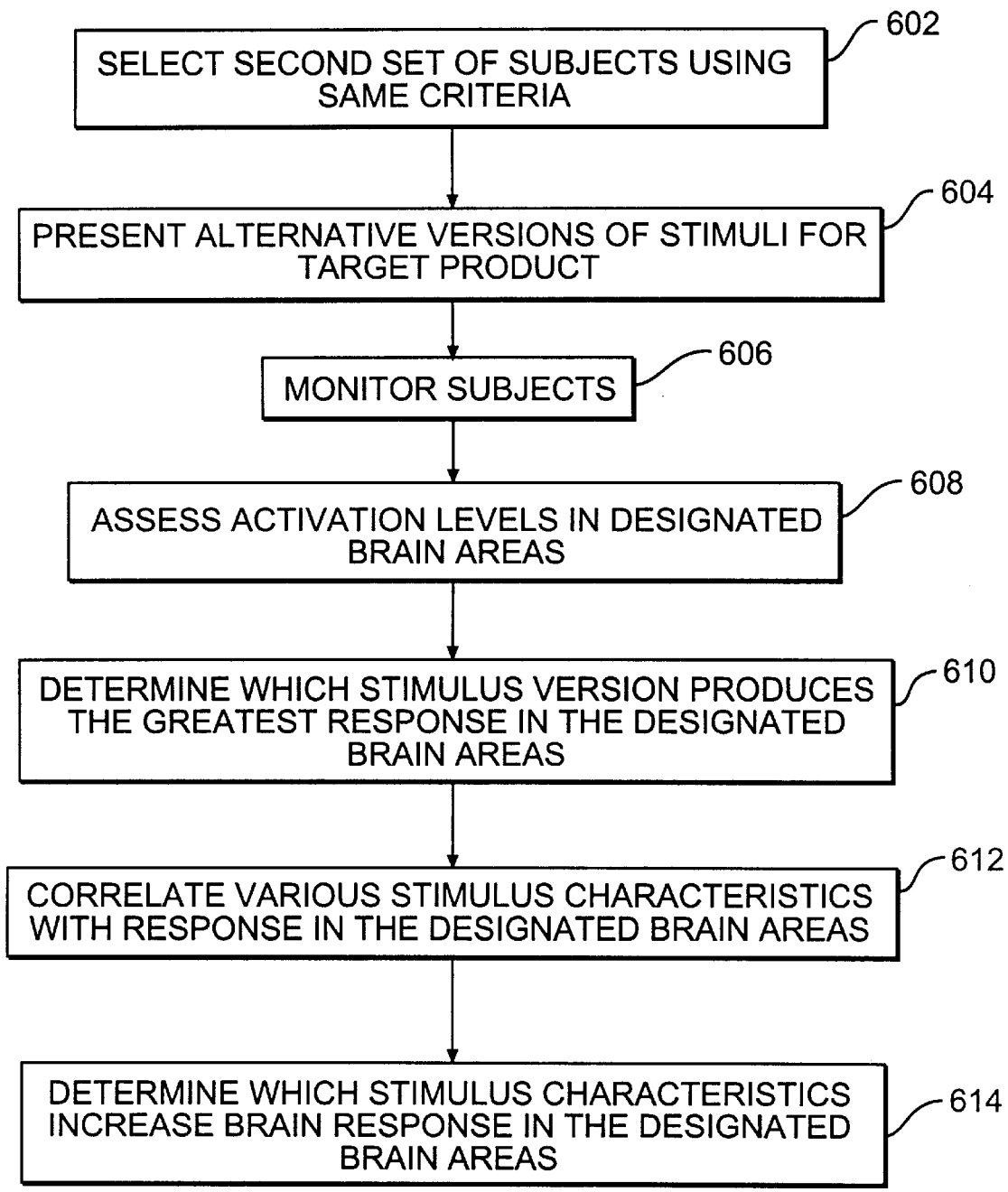
FIG. 6 illustrates the second phase of a prediction method.

FIGS. 5 and 6 illustrate a method designed to predict the effect of an advertisement or communication on later behavior, including consumption, preference and purchasing. This procedure involves two phases.

Phase One

FIG. 5 illustrates the first phase of the prediction method.

Subjects are selected 302 to be representative of a particular segment of the market. Thus, subjects are selected 302 on the basis of various characteristics, including but not limited to age, income level, gender, education, and place of residence. Results are thereby targeted to specific segments of the market.

Subjects are monitored 304 in a neuroimaging device while they are exposed to a stimulus communication. Neuroimaging devices include but are not limited to PET, fMRI, MEG, and SPECT. These devices all provide measurements of how active various brain areas become while the subject is exposed to a stimulus. The stimulus can be visual or auditory, or a combination of the two. Examples of stimulus which can be used include: an advertisement or communication about a target product.

At a predetermined later time, subjects return for further testing 502. In varying embodiments, the subjects travel to a different location to complete the further testing, and/or the subjects are not aware that the further testing is related to the previously conducted neuroimaging study. The predetermined time period between the neuroimaging study and the further testing is between several days to several months.

As a portion of the further testing a behavioral measurement is obtained 504. The subject is provided with an opportunity to interact with the product that was the subject of the stimulus presented during neuroimaging. Other similar products are also available to the subject. The preference shown to the subject of the stimulus as opposed to the similar product is surreptitiously measured thereby providing a behavioral measurement. In a preferred embodiment, this preference is measured by determining the amount of time spent with each product. For example, if the subject had previously seen advertisements for a magazine, that magazine and similar ones would be on the table in the waiting room, and a hidden videotape camera records how much time the subject spent looking at each magazine.

As another portion of the further testing, the subjects fill out questionnaires 506. The questionnaire can include but is not limited to ratings of emotional response to relevant items, questions about common activities, questions about past experiences with relevant products, and so on. Responses to the questionnaire can be timed, and the latencies can also be used as part of the analysis.

The measures of activation in a set of brain regions of interest are compared to the behavioral measures 508 using step-wise multiple regression analyses, where behavior is the dependent measure and the activation in different brain regions are the independent variables. This stepwise multiple regression analysis reveals the brain areas in which the amount of activation monitored during exposure to the stimulus predicts later behavior. For example, we might find that more blood flow in the left dorsolateral prefrontal area when subjects see an advertisement is positively correlated with how much time they later spend interacting with the product.

Phase Two

FIG. 6 illustrates the second phase of the prediction method.

Phase Two continues to build upon the results of Phase One. A different set of subjects from the same market segment 602 are presented with a series of alternative versions of the stimulus for the target product 604. Neuroimaging is used for each alternative version of the stimulus 606 to assess the activation levels in the brain areas that were identified in Phase One as predicting the behavior of interest 608. The version that produces the greatest response in the key brain areas is selected as most effective 610. For some applications, this is the goal. In addition, analyses of characteristics of the different versions of the stimulus, obtained from MET and similar techniques, are correlated with the brain responses 612. The result is discovery of what aspects of the advertisement or communication are driving the activation level of the key areas of the brain 614, and thereby resulting in the later behavior of interest.

Example: The Neural Correlates of Visualized Emotional Experiences: a PET Investigation This study explored the use of PET as a tool for strategic marketing research. PET measurements allow the researcher to draw inferences about the functions of particular regions of the human brain. Any given psychological process (e.g. forming a mental image, recalling a memory, solving a reasoning problem, learning to perform a behavior, generating an emotional response) requires increased or decreased processing within a specific subset of brain regions. Increased processing within a brain region requires a proportional increase in the concentration of oxygen and other blood-born metabolites required by that brain region. Thus, measuring the concentration of blood flow to different parts of the brain while an individual performs a task provides a means of measuring the relative processing contribution of each region of the brain to performance of the task.

This study examined whether PET can be utilized to reveal a set of "neural signatures" that correlate with valence (i.e. positive versus negative) and the intensity of emotional reactions generated in response to the imagined experience of alternative retail environments. Six right handed females between the ages of 18 and 35 listened to each of four scripts. Between each script the subjects filled out two inventories, one that was designed to assess the emotional feeling generated by their imagined experience and the other to assess the level of anxiety at that moment.

The baseline script described car dealership regulation policies in a hypothetical country. The language of this script was very technical and abstract, and thus did not lend itself to mental imagery as an effective means of interpretation.

Each of the three experimental scripts described a different car dealership in a way that was easy to visualize. The negative or stereotypical script describes a dirty, unorganized, socially intrusive, inconvenient environment, typical of many dealerships that currently exist. The neutral or "better dealership" script portrayed a nice retail environment that was organized, clean, convenient, and run according to a non-invasive sales technique. The positive or "very much better dealership" script described a state-of-the-art dealership that had all the positive features of the neutral dealership, but also provided the clients with accommodations that were comparable to a five-star restaurant, with emphasis on service and luxury.

Two points in the right dorsolateral prefrontal cortex were correlated to low valence ratings of the scripts. This region has been hypothesized to play a role in the "withdrawal" response. Thus, when confronted with an unappealing stimulus, such as a dirty, intimidating dealership, or the memory of this experience, the right dorsolateral prefrontal cortex becomes active and perhaps facilitates withdrawal from that situation.

In contrast, high ratings (where subjects reported liking a script more) covaried mainly with activation near the border of areas 18 and 19. This region is part of the secondary visual cortex and is involved in processing the images generated during visual mental imagery. When a scenario is thought of as pleasant, it invites subjects to engage their imagery systems to a greater degree, and the resulting visual images are more vivid and detailed.

A method and apparatus for using neuroimaging as a marketing tool has been described in detail for purpose of illustration. It is understood that such detail is solely for that purpose, and variations can be made therein by those skilled in the art without departing from the scope of the invention. The apparatus, operation and method of the present invention is defined by the following claims.

What is claimed is:

1. A method of evaluating stimulus materials comprising:
   selecting subjects;
   exposing the subject to stimulus materials;
   monitoring the subjects in a neuroimaging device while exposing the subjects to the stimulus materials;
   collecting data from the neuroimaging device; and
   analyzing the data.

2. The method of evaluating stimulus materials of claim 1, where the neuroimaging device is selected from the group of neuroimaging devices consisting of positron emission tomography, functional magnetic resonance imaging, magnetoencephalography and single photon emission computer tomography.

3. The method of evaluating stimulus materials of claim 1, where the stimulus materials are selected from the group of stimuli consisting of visual, auditory, and a combination of visual and auditory.

4. The method of evaluating stimulus materials of claim 1, further comprising:
   selecting subjects based on predefined parameters.

5. The method of evaluating stimulus materials of claim 4, where the predefined parameters are selected from the group of parameters consisting of age, income level, gender, education, and a combination thereof.

6. The method of evaluating stimulus materials of claim 1, where the stimulus materials are selected from the group of materials consisting of copy from an advertisement, description of a hypothetical environment, description of an actual environment, description of a hypothetical situation, description of an actual situation, description of a hypothetical behavior, and description of an actual behavior.

7. The method of evaluating stimulus materials of claim 1, further comprising:
   testing the subjects memory of the stimulus materials at a predetermined time period after exposing the subject to the stimulus materials.

8. The method of evaluating stimulus materials of claim 1, further comprising:
   monitoring the subject's behavior for a predetermined time period after exposing the subject to the stimulus materials.

9. A method of validating a questionnaire comprising:
   selecting subjects;
   exposing the subjects to stimulus materials;
   monitoring the subjects in a neuroimaging device while exposing the subjects to the stimulus materials;
   collecting data from the neuroimaging device;
   analyzing the data;
   providing the subject with a questionnaire which is completed by the subject;
   correlating the questionnaire responses with the analyzed data from the neuroimaging device.

10. The method of validating a questionnaire of claim 9, where the neuroimaging device is selected from the group of neuroimaging devices consisting of positron emission tomography, functional magnetic resonance imaging, magnetoencephalography and single photon emission computer tomography.

11. The method of validating a questionnaire of claim 9, where the stimulus materials are selected from the group of stimuli consisting of visual, auditory, and a combination of visual and auditory.

12. The method of validating a questionnaire of claim 9, further comprising:

selecting subjects based on predefined parameters.

13. The method of validating a questionnaire of claim 12, where the predefined parameters are selected from the group of parameters consisting of age, income level, gender, education, and a combination thereof.

14. The method of validating a questionnaire of claim 9, where the stimulus materials are selected from the group of materials consisting of copy from an advertisement, description of a hypothetical environment, description of an actual environment, description of a hypothetical situation, description of an actual situation, description of a hypothetical behavior, and description of an actual behavior.

15. The method of validating a questionnaire of claim 9, further comprising:

testing the subjects memory of the stimulus materials at a predetermined time period after exposing the subject to the stimulus materials.

16. The method of validating a questionnaire of claim 9, further comprising:

monitoring the subject's behavior for a predetermined time period after exposing the subject to the stimulus materials.

17. A method of predicting behavior comprising:

selecting a first set of subjects;

exposing the first set of subjects to stimulus materials;

monitoring the first set of subjects in a neuroimaging device while exposing the first set of subjects to stimulus materials;

collecting data from the neuroimaging device;

determining the measures of activation in a set of brain regions of interest from the collected data;

obtaining a behavioral measurement from the first set of subjects; and correlating the behavioral measurement with the measures of activation in the set of brain regions of interest.

18. The method of predicting behavior of claim 17 further comprising:

providing the first set of subjects with a questionnaire which is completed by the first set of subjects to yield questionnaire results; and correlating the questionnaire results with the behavioral measurement and the measures of activation in the set of brain regions of interest.

19. The method of predicting behavior of claim 18 further comprising:

selecting a second set of subjects;

monitoring the second set of subjects in a neuroimaging device while exposing the second set of subjects to a second type of stimulus materials;

collecting data from the neuroimaging device;

determining the measures of activation in a set of brain regions of interest from the collected data; and determining whether the stimulus materials or the second type of stimulus materials produces the greatest measures of activation in the set of brain regions of interest.

20. The method of predicting behavior of claim 19 further comprising:

analyzing characteristics of the stimulus materials and the second type of stimulus materials;

correlating the characteristics with the collected data.

21. The method of predicting behavior of claim 20 further comprising:

determining which of the characteristics produces the greatest measures of activation in the set of brain regions of interest.

* * * * *